(12) United States Patent
Zitzke

(10) Patent No.: US 10,321,716 B2
(45) Date of Patent: Jun. 18, 2019

(54) ELECTRONIC SMOKING DEVICE AND CAPSULE

(71) Applicant: FONTEM HOLDINGS 1 B.V., Amsterdam (NL)

(72) Inventor: Roland Zitzke, Bienenbuttel (DE)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 2 days.

(21) Appl. No.: 15/519,053

(22) PCT Filed: Oct. 12, 2015

(86) PCT No.: PCT/EP2015/073568
§ 371 (c)(1),
(2) Date: Apr. 13, 2017

(87) PCT Pub. No.: WO2016/058992
PCT Pub. Date: Apr. 21, 2016

(65) Prior Publication Data
US 2017/0215485 A1    Aug. 3, 2017

(30) Foreign Application Priority Data
Oct. 14, 2014   (EP) .................................. 14003520

(51) Int. Cl.
*A24F 13/00*    (2006.01)
*A24F 17/00*    (2006.01)
(Continued)

(52) U.S. Cl.
CPC ......... *A24F 47/008* (2013.01); *A61M 11/042* (2014.02); *A61M 15/008* (2014.02);
(Continued)

(58) Field of Classification Search
CPC ....................................................... A61M 15/06
(Continued)

(56) References Cited

U.S. PATENT DOCUMENTS

| 9,025,291 B2* | 5/2015 | Xiang | G06F 1/26 |
| | | | 361/93.1 |
| 2005/0081846 A1* | 4/2005 | Barney | A61M 15/0065 |
| | | | 128/200.23 |
| 2011/0036346 A1* | 2/2011 | Cohen | A61M 11/042 |
| | | | 128/200.14 |

(Continued)

OTHER PUBLICATIONS

European Patent Office, "Extended European Search Report", for EP3009017, dated Jul. 29, 2015, 9 pp.

(Continued)

*Primary Examiner* — Hae Moon Hyeon
*Assistant Examiner* — Thang H Nguyen
(74) *Attorney, Agent, or Firm* — Perkins Coie LLP; Kenneth H. Ohriner

(57) ABSTRACT

A capsule (6) contains a liquid (28) to be supplied to an atomizer (20) and is mounted on or in an electronic smoking device (1). The capsule (6) has a controller (40) including a memory, which receives data from and transmits data to control electronics (14) of the electronic smoking device (1). A capacitor in the capsule (6) is charged by the electronic smoking device (1) and powers the controller (40) during intermediate intervals. Electrical contacts (26, 48) of the capsule are connected to electrical contacts (24, 46) of the electronic smoking device (1) to charge the capacitor and exchange data.

19 Claims, 2 Drawing Sheets

(51) Int. Cl.
*A24F 25/00* (2006.01)
*A24F 47/00* (2006.01)
*A61M 15/06* (2006.01)
*A61M 11/04* (2006.01)
*A61M 15/00* (2006.01)
*A61M 15/02* (2006.01)
*A61M 16/00* (2006.01)

(52) U.S. Cl.
CPC ......... *A61M 15/06* (2013.01); *A61M 15/0035* (2014.02); *A61M 15/0085* (2013.01); *A61M 15/02* (2013.01); *A61M 2016/0015* (2013.01); *A61M 2205/3331* (2013.01); *A61M 2205/52* (2013.01); *A61M 2205/583* (2013.01); *A61M 2205/8206* (2013.01)

(58) Field of Classification Search
USPC ..................................... 131/329; 128/200.14
See application file for complete search history.

(56) References Cited

U.S. PATENT DOCUMENTS

| | | | |
|---|---|---|---|
| 2013/0220315 A1* | 8/2013 | Conley | A24F 47/008 128/202.21 |
| 2014/0060554 A1 | 3/2014 | Collett et al. | |
| 2014/0299137 A1* | 10/2014 | Kieckbusch | A24F 47/008 131/328 |
| 2015/0101625 A1* | 4/2015 | Newton | H05B 1/0244 131/329 |
| 2016/0050975 A1* | 2/2016 | Worm | A24F 47/008 131/328 |
| 2016/0219938 A1* | 8/2016 | Mamoun | G05B 15/02 |

OTHER PUBLICATIONS

European Patent Office, "International Search Report and the Written Opinion of the International Searching Authority", for PCT/EP2015/073568, dated Apr. 25, 2016, 14 pp.

* cited by examiner

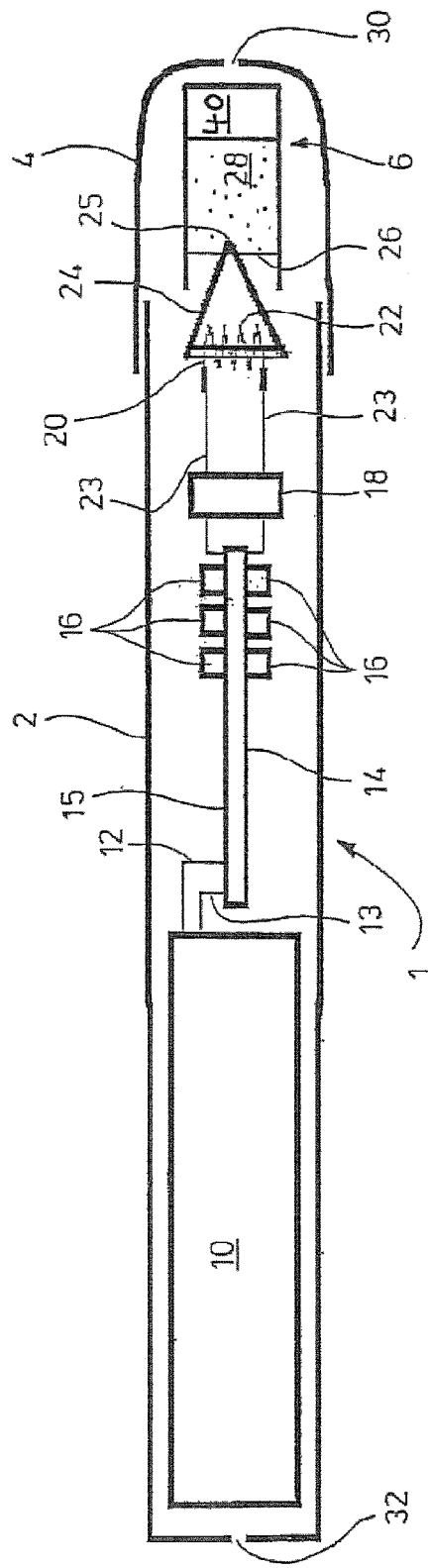
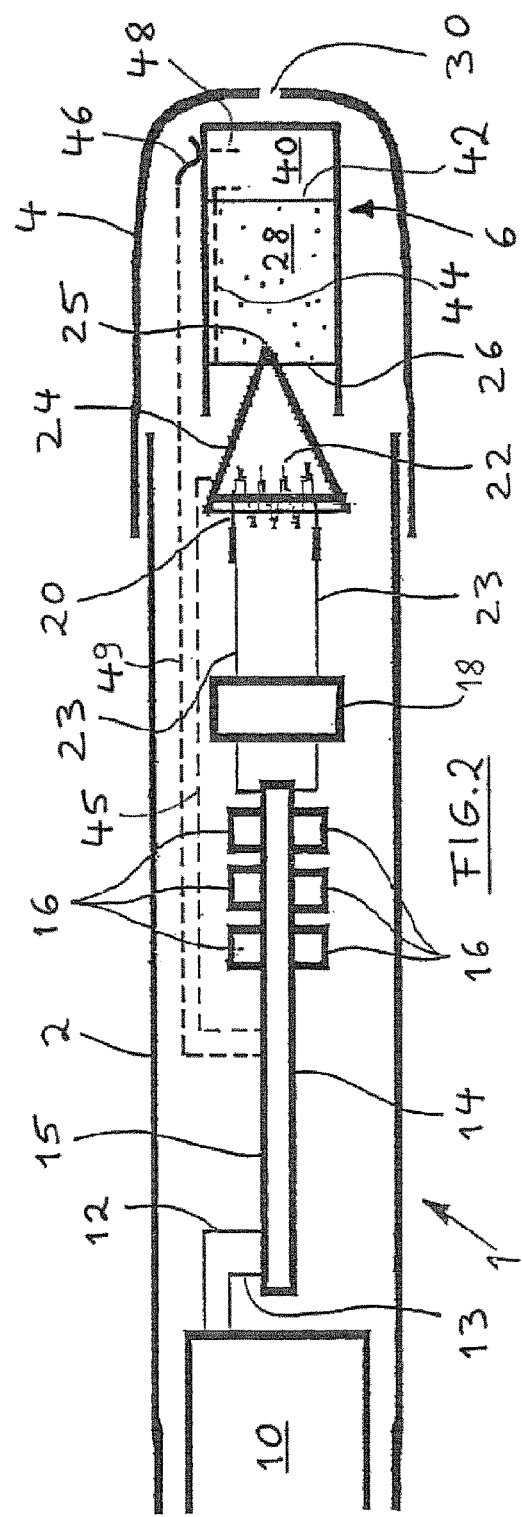
FIG.1
FIG.2

ELECTRONIC SMOKING DEVICE AND CAPSULE

BACKGROUND OF THE INVENTION

The present application relates to a capsule for an electronic smoking device and a system comprising an electronic smoking device and a capsule, which can be mounted to the electronic smoking device.

An electronic smoking device, such as an electronic cigarette, usually comprises a housing accommodating an electric power source (e.g., a battery), an atomizer including an electric heater adapted to atomize a liquid supplied from a reservoir or capsule into an aerosol, and control electronics which controls activation of the heater. A puff detector provided within the electronic smoking device is arranged to detect a user puffing on the device (e.g., by sensing an under-pressure or an air flow pattern through the device) and signals the puff to the control electronics. When a signal is detected the control electronics activates the atomizer, which creates an aerosol. The action of the atomizer is referred to as "atomizing" and the related product is called an "aerosol", irrespective of its composition, which might include gaseous and smoke constituents.

The capsule is usually disposable. This eliminates the risk for the user of contacting the liquid when refilling a non-disposable reservoir. With a disposable container or capsule, the user simply replaces the capsule as a whole when it is empty or when a different type of liquid is to be atomized.

However, the amount of liquid remaining in a capsule cannot easily be detected by the electronic smoking device, and the capsule cannot be authenticated.

Consequently engineering challenges remain in the design of electronic smoking device and capsule systems.

SUMMARY OF THE INVENTION

In a system including an electronic smoking device and a capsule, the electronic smoking device may have a housing, control electronics, and a puff detector. A battery (preferably a rechargeable battery) powers an atomizer which atomizes a liquid supplied from the capsule to provide an aerosol. The control electronics controls the atomizer. The puff detector indicates an aerosol inhaling puff to the control electronics. The capsule contains the liquid to be supplied to the atomizer and can be mounted in the electronic smoking device.

The capsule may include a controller (including a memory), which is able to receive data from the control electronics of the electronic smoking device and to transmit data to the control electronics. The capsule may have a capacitor which is charged by the electronic smoking device so that it can power the controller. The capsule may communicate with the electronic smoking device via a pair of electrical contacts connected to corresponding electrical contacts in or on the electronic smoking device.

The memory of the controller may be adapted to store the number of puffs taken from the capsule and/or to store an authenticity code. When the number of puffs taken is stored in the capsule, the capsule can be removed from the electronic smoking device (e.g. for temporarily replacing it with a capsule having a different flavour), while the system still has information on the actual amount of liquid in the capsule. If the capsule contains an authenticity code (which preferably is non-ambiguous), the capsule may be recognised by the control electronics of the electronic smoking device as a suitable capsule.

In some embodiments, the number of puffs taken from the capsule is not stored in the capsule but is instead stored in a memory of the control electronics of the electronic smoking device (e.g. in a memory addressed by a micro-controller). In this case the authenticity code of the capsule may be used for assigning a specific area of that memory to that particular capsule, and the number of puffs taken from that capsule is stored in that area. Similarly, another area of the memory can be used to store the number of puffs taken from a different capsule having a different authenticity code. In this way, e.g., capsules containing different flavors can be partially used, exchanged, and later on used again, while the control electronics of the electronic smoking device stays informed on the actual puff count of the individual capsules.

Generally, two electrical contacts are required to power the controller in the capsule via the battery of the electronic smoking device. On the other hand, to transmit digital information, a signal line has to be put to voltage levels representing two different states, e.g. ground voltage level for logical "0" and a distinctly different positive (or negative) voltage level for logical "1" or for separating ground voltage level signals of different duration. To achieve the supply of power and the transmission of data with a total of two electrical contacts only, a capacitor in the capsule may be used. The capacitor is charged by the electronic smoking device so that it can power the controller in the capsule during intermediate intervals, e.g. during intervals when the signal line is at ground voltage level during data transmission when it is not able to provide power to the controller.

The capsule may include a diode, which is adapted to prevent discharging of the capacitor when the capacitor powers the controller.

The controller of the capsule may include a timer, in particular a timer generating pulses of a predefined length and measuring the duration of pulses. If one of the electrical contacts of the capsule is defined as ground contact and the other electrical contact of the capsule is defined as signal contact (corresponding to the signal line above), the data transferred between the control electronics of the electronic smoking device and the controller of the capsule can be encoded as a sequence of voltage levels at the signal contact defined as ground level and high level. Preferably, the data are binary encoded as zero bits and one bits, wherein the control electronics of the electronic smoking device and the controller of the capsule are adapted to transfer a zero bit as a ground level signal for a preselected period and to transfer a one bit as a ground level signal for a different preselected period, wherein these ground level signals are separated by respective high level signals. In this case, the capacitor of the capsule can be charged when the voltage level at the signal contact is at high level, whereas the capacitor powers the controller when the voltage level at the signal contact is at ground level. Since, generally, there is no need for a rapid data transmission, the breaks between the ground level signals can be relatively long so that there will be sufficient time for charging the capacitor via the high level signals. Other schemes for binary-encoding the data may also be used.

The controller of the capsule may comprise a FET (field effect transistor), which is controlled by the controller and switches the signal contact to the ground contact when the voltage level is to be ground level.

The data transfer sequences and the information exchange can be controlled by the controller of the capsule in cooperation with the controller of the electronic smoking device, e.g. via firmware programs.

Generally, it is possible to keep the costs for the electronic components required in the capsule at a low level.

In some embodiments, the capsule may include a shell having an end side providing an access port, wherein the access port is closed by a pierceable membrane. The membrane may be a metal foil, which may optionally also serve as one of the electrical contacts. It is also possible that at least one of the electrical contacts is arranged at an outer face of the shell.

There are many ways for providing the electrical contacts.

For example, a non-conductive base material of the shell may be coated with a first conductive layer (or area) on the inside and a second conductive layer (or area) on the outside of the shell, which provides two electrical contacts isolated from each other. When inserting such a capsule into the electronic smoking device, the first conductive area of the shell may be contacted, e.g., by a metal part used for piercing the membrane (which, in this embodiment, can be non-conductive) in order to open a hole for passing the liquid. The second conductive area can be connected, e.g., via a support metal part holding the capsule.

The controller and the capacitor can be accommodated in an inner space of the capsule, preferably in an inner space separate from a reservoir which accommodates the liquid.

The battery and/or the atomizer may be components of the electronic smoking device.

Alternatively, in some embodiments an atomizer may be integrated in the capsule. In such embodiments, a third electrical contact may be provided at the capsule, for powering the heater of the atomizer, via the battery and the control electronics in the electronic smoking device. In this case, a first electrical contact serves as a ground contact (for connecting one terminal of the heater to ground as well as for data transfer), a second electrical contact as signal line for data transfer (see above) and the third electrical contact for connecting the other terminal of the heater to power. However, via circuitry in the capsule controlled by the controller, it is possible to use the second electrical contact both for data transfer and for powering the heater so that a total of two electrical contacts is sufficient in order for the device to operate.

BRIEF DESCRIPTION OF THE DRAWINGS

In the following, the invention is explained in more detail by the drawings which show examples.

FIG. 1 a schematic longitudinal section of an electronic smoking device and a capsule, FIG. 2 an enlarged schematic longitudinal section of the capsule of FIG. 1 and its electrical connections to the electronic smoking device and FIG. 3 a schematic block circuitry diagram illustrating the data communication between the controller of the capsule and the control electronics of the electronic smoking device.

DETAILED DESCRIPTION OF THE DRAWINGS

Figure 3:
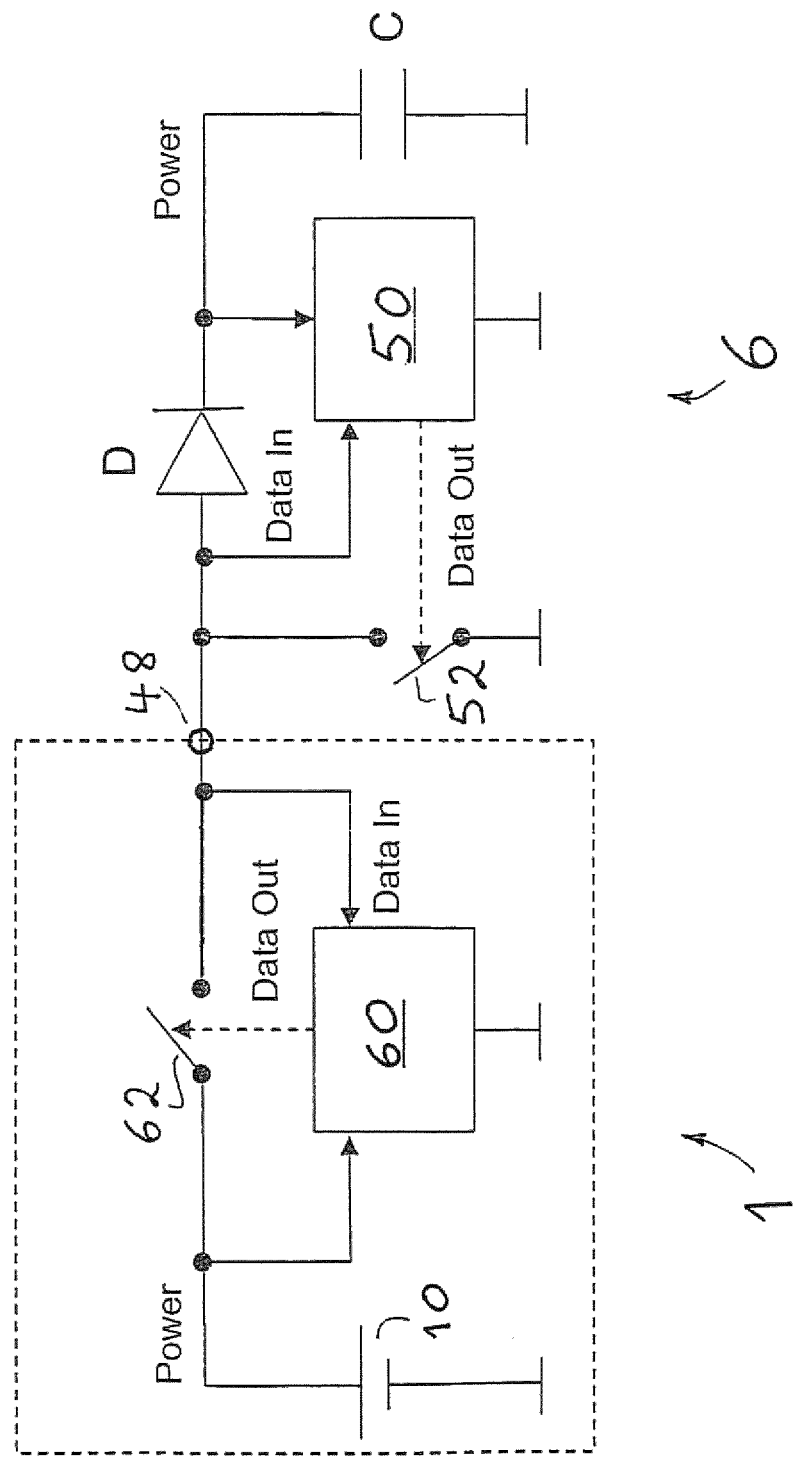

FIG. 1 illustrates an embodiment of a system comprising an electronic smoking device 1 and a capsule in a schematic longitudinal section.

The electronic smoking device 1 may include a cylinder-like housing 2 and a mouthpiece 4, which is designed as a detachable cap. Removing the mouthpiece 4 provides access to a replaceable capsule 6, which serves as a reservoir for a liquid and also contains an electronic controller.

The housing 2 holds a battery 10 which may be a re-chargeable battery, such as a lithium ion battery, with the battery 10 optionally including its own circuitry. The battery 10 is connected, via leads 12 and 13, to control electronics 14, which includes integrated circuits mounted on a printed circuit board 15. The printed circuit board 15 may also support light-emitting diodes (LEDs) 16 assembled behind respective windows provided in the housing 2 to indicate the current status of the electronic smoking device 1.

A puff detector 18 is connected to the control electronics 14. The puff detector 18 may be an inhalation sensor, which detects the vacuum generated inside the housing 2 when a user inhales at the mouthpiece 4.

In the example shown, an atomizer 20 has a heater 22 connected via leads 23 to the control electronics 14. The heater 22 includes a heating wire mounted at a ceramics shell which also supports a wick device 24 made of braided metal or sponge-like metal material. A piercing tip 25 at the distant end of the wick device 24 is able to penetrate a membrane 26 used for sealing the capsule 6 so that liquid 28 contained in the capsule 6 can be guided out of the capsule 6 and through the wick device 24 to the heater 22.

At its free end, the mouthpiece 4 has an inhalation aperture 30. At the opposite end of the electronic smoking device 1, a charging port 32 may be provided which permits re-charging of the battery 10, e.g. via a USB port.

In use, a fresh capsule 6 is inserted into the electronic smoking device 1 so that the membrane 26 is pierced and liquid is supplied from the capsule 6 via the wick device 24 to the the heater 22. When the user inhales at the inhalation aperture 30, the puff detector 18 senses the resulting vacuum inside the housing 2 and sends a corresponding signal to the control electronics 14. In response, the heater 22 is powered so that its heating wire atomizes the liquid to create an aerosol, which is inhaled by the user. The heater 22 remains switched on for a predetermined period of time.

The heater 22 may be provided in various other forms of direct heating and indirect heating of the liquid, each having advantages. In direct heating designs, the liquid directly contacts the heating element, which may be a wire coil, rod or other heater surface. In indirect heating designs, the liquid contacts a surface heated by a separate heating element, which does not come into direct contact with the liquid. Apart from the design shown in FIG. 2, the atomizer may include a heating wire wound around a fiber bundle, with the fiber bundle in contact with the wick 24, or with the fiber bundle forming the wick device. The fiber bundle may extend into the capsule.

Other types of atomizers or vaporizers may alternatively be used. Various ultrasonic atomizers are effective in creating vapour without heating. For example, an ultrasonic atomizer using a free-running Colpitts oscillator generates high-frequency energy in the range between 800 kHz and 2000 kHz driving a piezoelectric vibrator converting liquid into vapour. Atomizers having electrostatic, electromagnetic or pneumatic elements have also been proposed.

FIG. 2 is an enlarged view similar to FIG. 1 and illustrates that the capsule 6 may include an electronic controller 40, which is electrically connected to the control electronics 14 of the electronic smoking device 1 via two electrical contacts when the capsule 6 is mounted to the main body of the electronic smoking device 1. The capsule 6 may have a plastic shell, with the controller 40 inside of the shell separated from the liquid 28 by an intermediate wall 42.

One of the electrical contacts is provided by the membrane 26, which can be designed as a metal foil connected to the controller 40 via an internal lead 44. The internal lead 44 may be passed through the liquid 28, as shown in FIG. 2, or may be guided, e.g., through a duct at the outer face of the capsule 6. Another lead 45 connects the metallic wick device 24 including its piercing tip 25 to the control electronics 14, as shown in FIG. 2. Thus, when the capsule 6 is inserted into the electronic smoking device 1 and the piercing tip 25 has penetrated the membrane 26, an electrical connection from the control electronics 14 of the electronic smoking device 1 to the controller 40 of the capsule 6 is established.

The other electrical contact may be provided by a contact spring 46, which abuts to a small metallic contact area 48 at the otherwise non-metallic outer face of the capsule 6. The metallic contact area 48 is connected to the controller 40, as shown in FIG. 2. The contact spring 46 is connected to the control electronics 14 of the electronic smoking device 1 via a lead 49.

These two electrical contacts are sufficient to power the controller 40 of the capsule 6 and to permit data communication between the controller 40 and the control electronics 14 of the electronic smoking device 1. FIG. 3 shows a schematic block circuitry diagram illustrating this data communication. One of the electrical contacts, e.g. that one provided via the pierced membrane 26, is indicated by the ground symbol, the other one by reference numeral 48 mentioned above. The components inside the dashed box are included in the electronic smoking device 1, the other ones in the capsule 6.

The controller 40 of the capsule 6 may have a processor 50 including a memory. The processor 50 is powered by the battery in the electronic smoking device 1 or by a capacitor C mounted in the capsule 6, depending on the state of operation, as explained below. During data transfer, the processor 50 controls an electronic switch 52 (e.g., a FET).

The control electronics 14 of the electronic smoking device 1 includes a processor 60, which can actuate an electronic switch 62. When switch 62 is closed, the capacitor C is charged. Whenever switch 62 is closed, switch 52 is open. FIG. 3 further indicates the lines of data flow.

The communication (data transfer) between the main unit represented by the control electronics 14 in the electronic smoking device 1 and the controller 40 in the capsule 6 can be established by applying the following general method:

Communication is initiated by the main unit, i.e. the electronic smoking device 1. In order to initiate communication, the processor 60 sends a long pulse ("Data Out") by closing switch 62 so that power is supplied to contact 46/48 and the capacitor C in the capsule 6 is charged. The long pulse is long enough to charge the capacitor sufficiently, e.g. 100 ms.

Afterwards, the main unit can send information in a binary encoded form wherein "1" and "0" are represented by electrical levels, e.g. a "0" is represented by no power (i.e. switch 62 open) while a "1" is indicated by supplying power (i.e. switch 62 closed) and wherein, e.g., all the pulses have the same length. The end of communication can be marked with a power-on pulse of a different duration. Alternatively, information may be sent by representing "1" and "0" by different power-on durations, with power-off phases in between for separating these pulses. The power-off phases (i.e. switch 62 is open) are kept short, e.g. no longer than 2 µs, because during these phases the capacitor C is not charged and rather serves as the power supply for the controller 40 in the capsule 6.

The processor 50 of the controller 40 sends information to the main unit by using the switch 52 ("Data Out"). When the switch 52 is closed, the voltage level at contact 46/48 drops to virtually ground level, which is received by the processor 60 ("Data In"). During this phase, switch 62 is open to prevent a short, and the capacitor C powers the processor 50 while the diode D prevents the capacitor C from discharging. As soon as the switch 52 is opened again, the voltage level at "Data In" of the processor 60 rises and the capacitor C is charged again. In other words, the battery 10 of the main unit supplies limited power such that the capacitor C in the capsule 6 is charged, but the processor 50 is also able to create ground level pulses by using the switch 52. In this way, the processor 50 and the switch 52 can create a sequence of pulses, e.g. ground level pulses of two different durations for representing "1" and "0" which are separated by high level pulses also charging the capacitor C.

As described, this design provides communication between the electronic smoking device 1 and the capsule 6 via just two electrical contacts.

The electronic switch 52 in the controller 40 of the capsule 6 may be implemented as a field effect transistor (FET). The processor 50 including its memory maintains a persistent puff counter for the purpose of communicating the fill status of the liquid 28 to the control electronics 14 of the electronic smoking device 1 (main unit). The puff counter can be represented by an 8-bit number which is automatically incremented each time the main unit initiates a communication. This increment is performed by the processor 60 in the capsule 6.

When the puff detector 18 of the electronic smoking device 1 senses a puff, the main unit initiates a communication. To this end, the processor 60 closes the switch 62 to send a high-level pulse of 100 ms to charge the capacitor C. The processor 60 ends that pulse by opening switch 62 and leaves a 20 µs gap with no power before closing switch 62 again and waiting for pulses generated by the capsule 6. The processor 50 first increments the puff counter by one and then communicates the actual puff count to the processor 60 by means of an 8-bit number. To transmit the 8-bit number, in the example, switch 52 is closed for 1 µs for a "0" to be sent and for 5 µs for a "1" to be sent, leaving it open for 10 µs or longer between each binary digit to provide for sufficient time for recharging the capacitor C.

In this way, the 8-bit number is received at the "Data In" port of the processor 60 of the main unit. The processor 60 measures the duration of the ground level pulses to decode the individual binary digits and stores the 8-bit number as the actual puff count of capsule 6.

In case the capsule 6 is removed from the electronic smoking device 1 and later on mounted again, the system will know about the number of puffs already taken from capsule 6.

If the actual puff count has reached a predetermined maximum number stored in processor 60, the capsule 6 is empty or almost empty, which can be signalled to the user, e.g., via a certain pattern of illumination of the LEDs 16.

In the above example, the actual puff count is the data to be transferred between the electronic smoking device and the capsule. Other data might be exchanged as well, for example an authentication code of the capsule (e.g. transmitted by the capsule as leading data just before the latest puff count is transmitted to the electronic smoking device).

In embodiments where an authentication code is stored and transmitted by the capsule 6, the control electronics 14 of the electronic smoking device 1 may be arranged to inhibit the activation of an atomiser 20 if an invalid authentication codes is received. Thus in this way the electronic smoking device 1 could be prevented from interacting with unauthorised or out of date capsules.

From the above description it will be appreciated that the inclusion of electrical contacts 26, 48 and a controller 40 within a capsule 6 for mounting on an electronic smoking device 1 can give rise to a number of different advantages depending on the use of data stored utilised by the smoking device 1. In the above description, both the monitoring of the use of a capsule 6 and the confirmation of the authenticity of a capsule 6 have been described. Other embodiments might utilise the transfer of data in other ways.

Although data is stored within a memory within a controller 40 on the capsule 6, no power source is provided within the capsule itself which reduces the complexity of the capsule 6. Rather, as described the power source for the controller 40 is ultimately provided by the battery 10 of an electronic smoking device. This minimises the complexity of the capsule 6 and reduces manufacturing costs.

The complexity of the capsule 6 is reduced by utilising the metal foil enclosing a capsule 6 as one of the electrical contacts for incorporating the controller 40 within an electrical circuit and connecting the controller 40 with the battery 10 and/or the control electronics 14. Further as described in the above embodiments the same electrical contacts are utilised both to transfer data and provide an electrical circuit for powering the controller 40 present on the capsule 6.

Although a specific data transfer scheme has been described enabling data to be transferred between a capsule 6 and an electronic smoking device 1, alternative data transfer schemes could of course also be utilised. The data signalling schemes selected should be designed within the limitations of powering a controller 40 of a capsule 6 via the capacitor C. Thus for example it is preferable that suitable data transfer schemes might involve an initial period of higher voltage when first communicating so that the initial start signal might be utilised to charge the capacitor C. Further it is preferable that power off phases should be kept short as during such phases the power needs for the controller 40 are provided through the discharge of the capacitor C.

The capacitance C of the capacitor C required to power the capsule 6 during power off phases in data transfer can be roughly estimated in the following way: Assuming a nominal voltage of the battery 10 of 3.7 V and assuming that the communication electronics 50, 52, 60, 62 tolerates voltages between 3.7 V and 2.7 V, an acceptable voltage drop is $\Delta V=1$ V. Further assuming that the communication electronics consumes a current of about I=2 mA and that a low-pulse duration T during which the capacitor C has to power the capsule 6 is less than 500 µs, the required capacitance C follows from $$I \cdot T = C \cdot \Delta V \text{ or}$$

$$C = I \cdot T / \Delta V = 1 \text{ µF}.$$

A capacitor of a capacitance C in the order of 1 µF fits into the limited space available in the capsule 6. 1 µF is significantly more than a usual capacitance of a signal-shaping capacitor. The above figures are to be understood as an illustrative example only, not in a limiting sense.

Thus, a novel electronic smoking device and capsule system and related methods have been shown and described. Various changes and substitutions may of course be made without departing from the spirit and scope of the invention. The invention, therefore, should not be limited, except to the following claims and their equivalents.

The invention claimed is:

1. A capsule for use with an electronic smoking device having control electronics and an atomizer to atomize a liquid, comprising:

first and second electrical contacts, which are adapted to be connected to electrical contacts provided at the electronic smoking device;

a controller including a memory, wherein said controller is operable to exchange data with the control electronics of an electronic smoking device via said first and second electrical contacts when said first and second electrical contacts are connected to electrical contacts provided at the electronic smoking device; and a capacitor electrically connected to the controller and to the first and second electrical contacts, adapted to be charged by the electronic smoking device when the first and second electrical contacts are connected to electrical contacts provided at the electronic smoking device and to power the controller during intermediate intervals.

2. The capsule of claim 1, wherein the memory of the controller is adapted to store the number of puffs detected by a puff detector of an electronic smoking device whilst the capsule is mounted to the electronic smoking device.

3. The capsule of claim 1 wherein the memory of the controller is adapted to store an authenticity code.

4. The capsule of claim 1 wherein the capsule comprises a diode, which is adapted to prevent discharging of the capacitor when the capacitor powers the controller.

5. The capsule of claim 1 wherein the controller includes a timer.

6. The capsule of claim 5, wherein the first and second electrical contacts of the capsule are adapted to contact a ground contact and a signal contact of an electronic device when the capsule is mounted to the device and to receive and transmit data between the control electronics of the electronic smoking device and the controller of the capsule encoded as a sequence of voltage levels.

7. The capsule of claim 6, wherein the data comprises binary encoded as zero bits and one bits and in that the control electronics of the electronic smoking device and the controller of the capsule are adapted to transfer a zero bit as a ground level signal for a preselected period and to transfer a one bit as a ground level signal for a different preselected period, wherein these ground level signals are separated by respective high level signals.

8. The capsule of claim 6 wherein the capacitor of the capsule is adapted to be charged when the voltage level at a signal contact is at high level and is adapted to power the controller when the voltage level at the signal contact is at ground level.

9. The capsule of claim 6, wherein the controller of the capsule comprises a FET controlled by the controller and adapted to switch a signal contact to the ground contact when the voltage level is to be ground level.

10. The capsule of claim 1, wherein the capsule comprises a shell having an end side providing an access port, wherein the access port is covered by a pierceable membrane.

11. The capsule of claim 10, wherein the membrane comprises a metal foil and the metal foil serves as one of the first and second electrical contacts of the capsule.

12. The capsule of claim 10, wherein at least one of the first and second electrical contacts of the capsule is provided at an outer face of the shell.

13. The capsule of claim 1, wherein the controller and the capacitor of the capsule are accommodated in an inner space of the capsule, separate from a reservoir which is operable to accommodate liquid for atomisation.

14. The capsule of claim 1, further comprising an electrically heatable atomizer integrally provided with the capsule and operable to atomize a liquid supplied from a reservoir in an inner space of the capsule which is operable to accommodate liquid for atomisation.

15. An electronic smoking system comprising:
an electronic smoking device comprising:
a housing adapted to accommodate a battery for powering an electrically heatable atomizer;
control electronics adapted to control an atomizer for atomising liquid supplied from a capsule mounted to the device; and
a puff detector adapted to indicate an aerosol inhaling puff to the control electronics of the electronic smoking device;
the capsule including:
first and second electrical contacts adapted to be connected to device electrical contacts on or in the electronic smoking device;
a controller having a memory, wherein the controller is operable to exchange data with the control electronics of the electronic smoking device via the first and second electrical contacts when the first and second electrical contacts are connected to the device electrical contacts; and
a capacitor electrically connected to the controller and to the first and second electrical contacts, the capacitor adapted to be charged by the electronic smoking device when the first and second electrical contacts are connected to device electrical contacts and to power the controller at intervals.

16. A capsule for use with an electronic smoking device, comprising:
a capsule housing;
a liquid supply and capsule electronics in the housing separated by an intermediate wall, with the capsule electronics including a controller having a memory, and a rechargeable power source; and
electrical contacts on the housing for electrically connecting the capsule with electronic control circuitry in an electronic smoking device.

17. The capsule of claim 16 with the liquid sealed off from the electronics by the intermediate wall.

18. The capsule of claim 16 wherein the capsule is a non-refillable single use container including a frangible or pierceable seal sealing the liquid into the capsule, wherein the frangible or pieceable seal is pierceable by a piercing tip of an electronic smoking device.

19. The capsule of claim 16 further comprising an electronic cigarette having a housing with diameter of 10 mm or less and a length of 120 mm or less, and with the capsule dimensioned to fit in the electronic cigarette housing.

* * * * *